United States Patent [19]

Ball

[11] Patent Number: 4,815,151
[45] Date of Patent: Mar. 28, 1989

[54] URINARY GUIDE APPARATUS AND METHOD OF USING THE SAME

[76] Inventor: Dianne M. Ball, P.O. Box 8018, Incline Village, Nev. 89450

[21] Appl. No.: 39,387

[22] Filed: Apr. 17, 1987

[51] Int. Cl.4 .......................................... A47K 11/00
[52] U.S. Cl. ....................................... 4/144.3; 4/144.1; 4/144.2; 4/144.4; 604/347; 604/349
[58] Field of Search .......................... 4/144.1–144.4, 4/301, 114.1, 450, 452, 454, 462, 463, 455, 456; 604/347, 329, 350

[56] References Cited

U.S. PATENT DOCUMENTS

| | | | |
|---|---|---|---|
| 1,761,609 | 6/1930 | Becker | 604/350 X |
| 1,928,170 | 9/1933 | Dwork | 4/144.4 |
| 2,944,551 | 7/1960 | Breer | 604/347 X |
| 3,000,015 | 9/1961 | Hart | 4/144.3 |
| 3,116,734 | 1/1964 | Terman | 604/329 |
| 3,194,238 | 7/1965 | Breece, Jr. | 604/329 |
| 3,349,768 | 10/1967 | Keane | 604/347 |
| 3,526,227 | 9/1970 | Appelbaum | 604/350 |
| 3,528,423 | 9/1970 | Lee | 4/144.3 X |
| 3,547,123 | 12/1970 | Sachs | 604/350 X |
| 3,707,969 | 1/1970 | Sanford | 604/347 |
| 3,995,329 | 12/1976 | Williams | 4/144.3 |
| 4,421,511 | 12/1983 | Steer et al. | 4/144.3 X |
| 4,496,355 | 1/1985 | Hall et al. | 4/144.3 X |
| 4,568,339 | 2/1986 | Steer | 4/144.3 X |
| 4,583,983 | 4/1986 | Einhorn et al. | 604/329 X |
| 4,615,692 | 10/1986 | Giacalone et al. | 604/329 X |

FOREIGN PATENT DOCUMENTS

| | | | |
|---|---|---|---|
| 378760 | 10/1907 | France | 4/144.3 |
| 996370 | 6/1965 | United Kingdom | 4/144.3 |

*Primary Examiner*—Henry K. Artis
*Attorney, Agent, or Firm*—Richard C. Litman

[57] ABSTRACT

An apparatus for guiding the flow of urine from a female is disclosed. It includes a urinary-guide unit which is shaped to the contours of the female genital region and constructed of one-piece, flexible material, secured in place manually or by means of specially constructed garments which can be used to store the unit when the unit is intended to be worn. The method of using this apparatus is also disclosed.

12 Claims, 3 Drawing Sheets

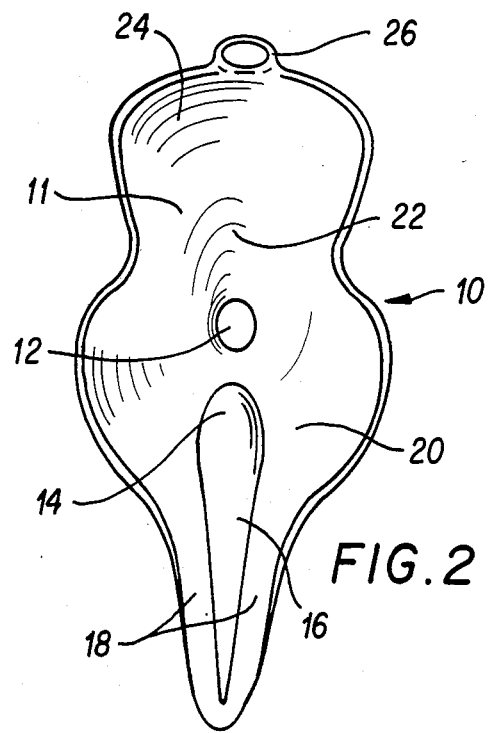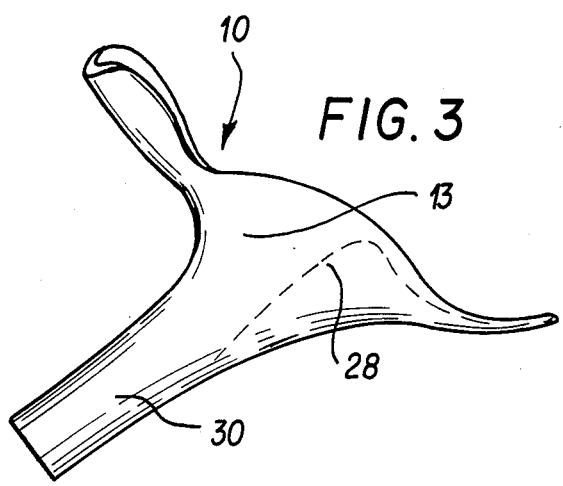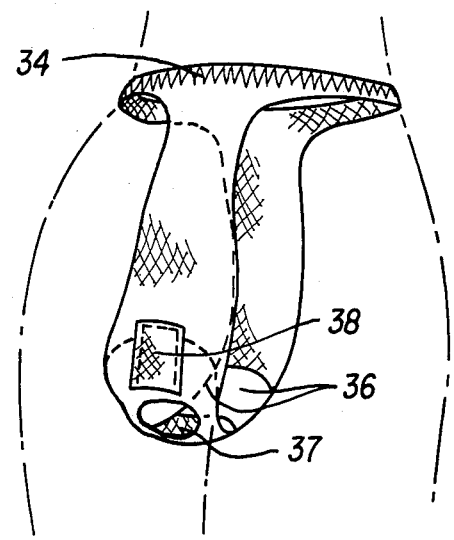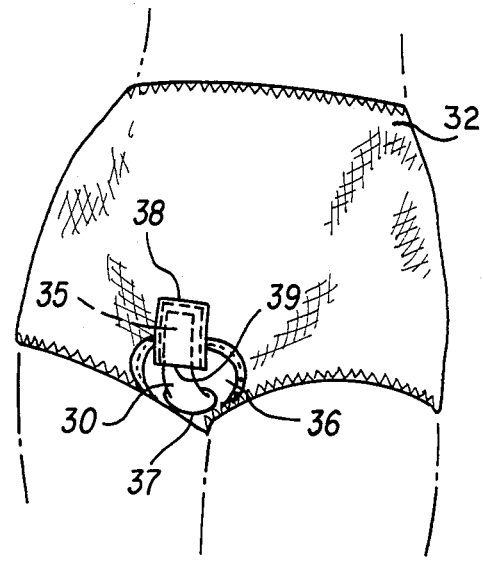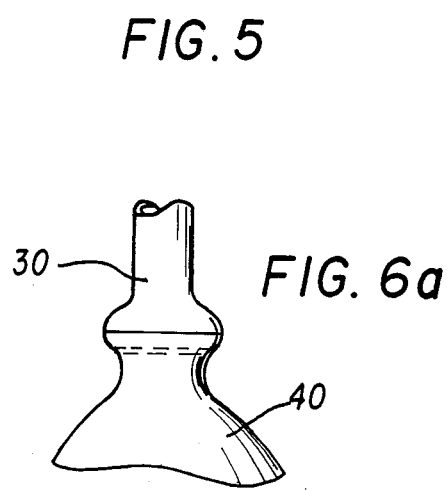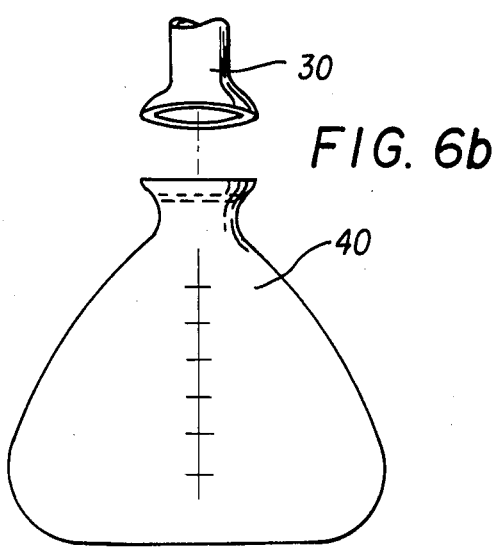

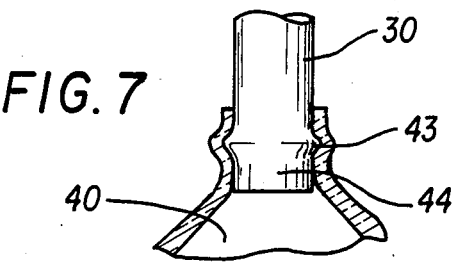
FIG. 7
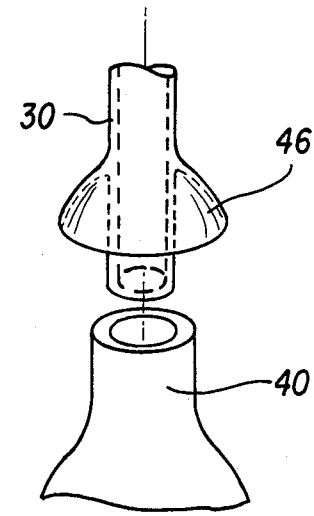
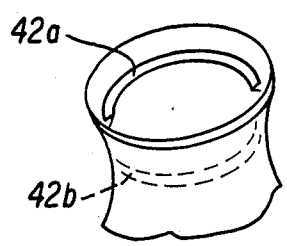
FIG. 6c
FIG. 6d
FIG. 8
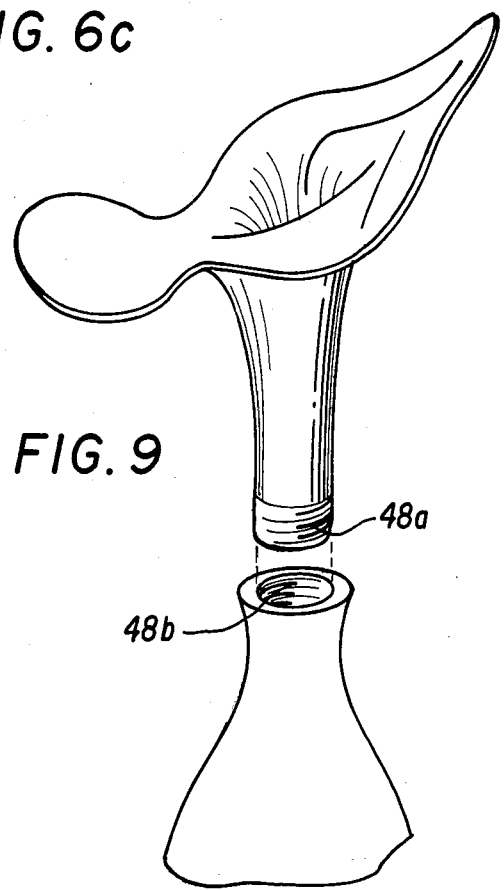
FIG. 9
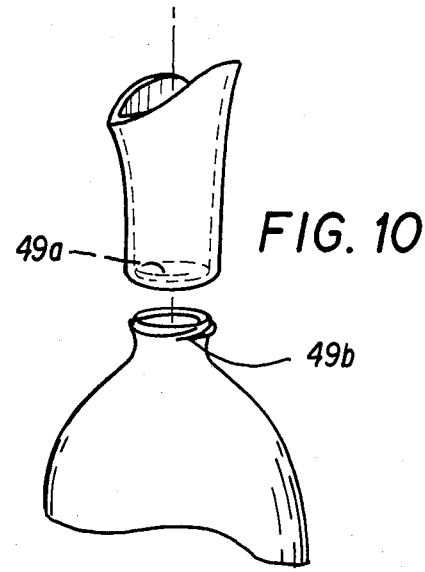
FIG. 10

URINARY GUIDE APPARATUS AND METHOD OF USING THE SAME

BACKGROUND OF THE INVENTION

In our active society, many vocational and avocational activities require the participant to engage in the activity for extended time periods, thus not permitting an individual the opportunity to urinate when the need arises. Males have used various receptacles for this purpose, but females, because of the anatomy of their genital region, have been unable to use these devices, and thus have experienced much inconvenience. The apparatus of this invention enables the female user to urinate into various receptacles (or outdoors) while engaged in work or recreational activities or when medical need requires, and the invention provides a convenient garment attachment for wearing with a contoured, urinary-guide unit of the invention which is shaped so as to conform to the contours of the female genital anatomy.

This invention also allows the female the freedom to urinate while in a standing or other nonsitting position. This is particularly relevant in today's society where many public restrooms are unsanitary and women fear acquiring a communicable disease from using these facilities. Women can easily use the one-piece, urinary-guide unit of the invention which is shaped so as to conform to the contours of the female genital anatomy, securing it in place for use either with their hands or by means of the specially constructed garments.

More particularly, this invention relates to an apparatus utilized by females to urinate, and consists of a flexible, molded, one-piece, urinary-guide unit which is shaped so as to conform to the contours of the female genital anatomy, where it is positioned to direct the flow of urine through a flexible member. The apparatus can be worn when stored in an undergarment designed to secure the unit to the user, with the flexible member portion held in position against the body when the device is not in use. The specially constructed shape of the unit prevents infection to the vagina caused by bacterial growth resulting from urine leakage from the urethra, and prevents urine from splashing on the user or her clothes during urination.

PRIOR ART

Various techniques and devices have been employed to enable a female to urinate in a nonsitting position. Some of these methods require a woman to wear an absorbent pad, similar to feminine napkins. Other techniques are invasionary in nature, requiring the insertion of the device into the urethra. Yet other apparatuses involve the use of an intricate device to control the stream of urine for collection or for disposal in a urinal or toilet. They are:

| U.S. Pat. No. | Inventor |
|---|---|
| 2,467,585 | Bernard Cohen |
| 2,522,008 | Beatrice Wohlman |
| 2,522,009 | Beatrice Wohlman |
| 2,852,780 | George Gold |
| 3,224,448 | George L. Diebold |
| 3,398,739 | Nicholas A. Marino |
| 3,864,759 | Akira Horiuchi |
| 4,023,216 | Laurie Rhea Li |
| 4,270,539 | Michaud (NASA) |
| 4,528,703 | Richard J. Kraus |

-continued

| U.S. Pat. No. | Inventor |
|---|---|
| 4,608,046 | Keivan Towfigh |

Urinary aid devices that work in conjunction with panty-type and belt-type garments are known in the prior art. The Michaud (NASA) patent discloses a collection device for females which provides a garment for supporting such a device. However, the shape of the urine collection device does not precisely conform to the contours of the genital region of the user, and the rigid structure of the collection device does not entirely prevent leakage. Also, the panty-type garment does not have an exact means of supporting the rigid structure of the collection device.

U.S. patents to Hall and Einhorn disclose urinary devices to be used with belt-type garments. The drainage devices of these patents are not entirely shaped so as to fit the specific contours of the female genital region, and, thus, the belt-type garments do not altogether properly support the drainage devices disclosed.

The above referenced patents disclose urinating devices and devices with garments of various sorts and of various manufacturers, and the like, as well as the methods of their construction; but none of them whether taken singly or in combination, discloses the specific details or combination of the invention in such a way as to bear upon the claims of the present invention.

No prior art has been located which describes the combined features of the urinary-guide apparatus of the invention. None of these prior devices or methods employs the combination of components of the present invention, namely, a noninvasive, one-piece, molded-guide unit made of flexible, semirigid material, which can be cleaned and reused, or of a molded papar or paper-like material intended for disposal after one use, which contours to the female anatomy, and which may be secured and stored in specially constructed garments.

SUMMARY OF THE INVENTION

One object and advantage of this invention is to provide the female with an easily useable device for urinating in a non-sitting position.

Another object is to provide a novel construction for a device contoured to the female anatomy so as to prevent leakage, which leaves stains on clothing and may cause disease.

Another object of the invention is to provide a reusable device which can be secured and stored in specially constructed garments or stored on a hook.

Another object of the invention is to provide the female with a convenient means to urinate into male-urine receptacles or other specially designed receptacles of the invention, or outdoors.

Another object of the invention is to provide a garment which can be aesthetically worn, yet effective in securing the associated urine-guide unit or storing it when not in use.

Another object of the invention is to provide a method by which the female can effectively utilize the apparatus of the invention without difficult procedures.

These objects, together with other objects and advantages of the invention, reside in the details of the construction and the operation thereof, as is more fully hereinafter described and claimed. References are made to drawings forming a part thereof, wherein like numerals refer to like parts throughout.

BRIEF DESCRIPTION OF THE DRAWINGS

FIG. 2 is a top view of the surface of the invention.

FIG. 3 is a side view of the invention.

FIG. 4 is a front view of the invention, showing the unit secured by a panty undergarment.

FIG. 5 is a front view of a strapped undergarment used to secure the invention.

FIG. 6a shows one embodiment of the invention wherein the unit is manufactured as a one-piece, disposable unit and snapped apart (FIG. 6b) after the specimen has been collected.

FIGS. 6c and 6d show another embodiment of the invention wherein the receptacle can be sealed by employment of a ridge-and-slot type zipper.

FIG. 7 shows another embodiment of the invention wherein the member and receptacle are sealed by employment of a squeeze-lock type seal.

FIG. 8 shows another embodiment wherein the flexible member has a dish-shaped head.

FIG. 9 shows a further embodiment wherein the member is threaded externally and the receptacle is threaded internally.

FIG. 10 shows another embodiment of the invention wherein the member is threaded internally and the receptacle is threaded externally.

DETAILED DESCRIPTION OF THE PREFERRED EMBODIMENTS

Figure 1:
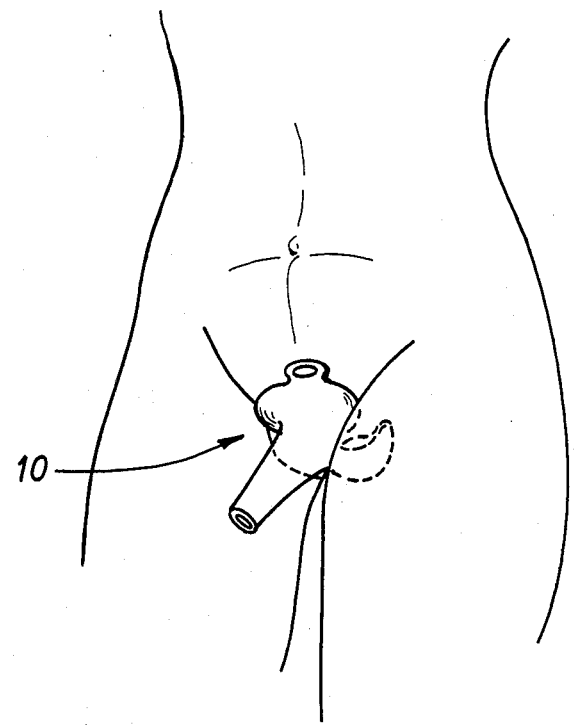
FIG. 1 is a perspective view of the invention manually secured in place by the user.
Figure 1A:
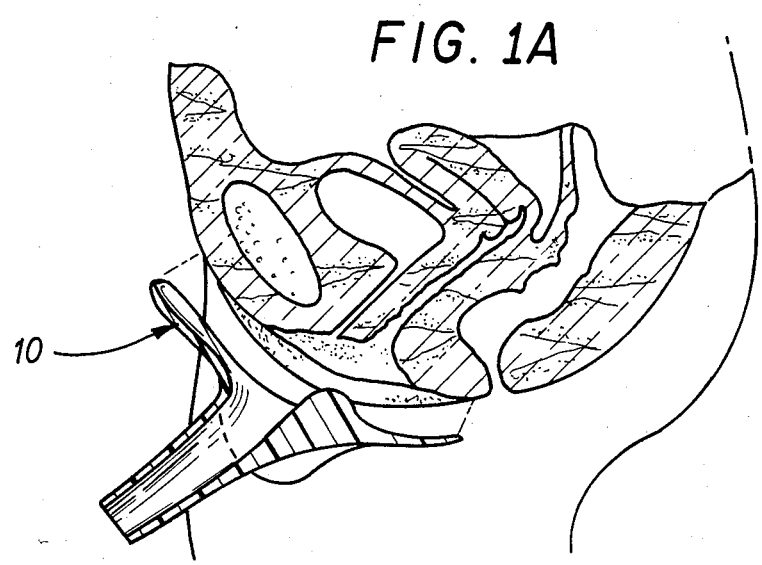
FIG. 1a is an exploded view of the invention contoured to the anatomy of the genital region of the user.

Referring now to the drawings, FIG. 1 shows the one-piece, contoured, urinary-guide unit 10 of the invention which is shaped so as to conform to the contours of the female genical region and is secured to the female user by the user's hand. FIG. 1a shows the invention as it contours to the user's genital region.

FIGS. 2–3 show the general cup-shaped inside surface 11 and unit 10 which is shaped to the contours of the female genital anatomy. Although various sizes are contemplated, such as for infants and preteenage girls, the surface 11 of the unit 10 has a single enlarged opening therein called a urethral orifice 12 by which urine passes from the user's external urethral orifice into flexible member 30 for collection or disposal. As will be seen the walls of the inside surface 11 surrounding the orifice 12 are downwardly dished to encourage the passage of the fluid toward the orifice. Orifice 12 is secured to the area of the user's urethral orifice in such an alignment that urine does not pass beyond the edges of orifice 12 into the vagina or onto the user or her clothes.

This alignment is due to the other contour features of the inside surface 11. Vaginal cover 14 will be seen to comprise an elongated rearwardly projecting protuberance directly beneath orifice 12, at a distance generally equal to the distance between the external urethral orifice and the vaginal opening or orifice of the user. The vaginal cover 14 positioned against the vaginal opening forms a seal around the cover 14 once it is situated and properly occludes the vaginal orifice to prevent urine contamination of the vaginal opening. The base of vaginal cover 14 forms the anterior edge of vaginal ridge guide 16. Guide 16 is a vertical elevation which is shaped to the contours of a female's lower vaginal orifice and frenulum of the user. It slopes at a gradual decline and adjoins both the left and right groin contour regions 18. Said regions 18 are shaped so that they will conform to the respective contours of the user's labium majus. The labium majus is a thick body of tissue that provides a means of support for unit 10. Left and right regions 18 converge at orifice 12; surrounding orifice 12 is the labial contour region 22 which is a depression in the inside surface 11 to conform with the anatomy of the labium minus. The left and right regions of the labium minus comfortably rest on the depressed areas of the labial contour region 22 when unit 10 is in use. The bottom of the unit, which is shaped to the contours of the perineum region of the external genital organs of the female to support unit 10, is called the base contour region 20, and the top of the unit, the pubic contour region 24, is shaped to conform to the contours of the user's public bone.

FIG. 3 shows a side view of the outside surface 13 of unit 10, showing the flexible member 30, which, in one embodiment, is approximately 4 inches long and ¾ to 1 inch in diameter. Like the other regions of the unit, it is constructed of a flexible, material composed of rubber, plastic, or similar synthetic material. This material may conduct heat in such a manner as to be comfortable to the touch when worn and could be of a hypoallergenic or similarly nonirritating nature. Flexible member 30 is easily bent into its desired position, either for use or storage. This is characterized by a gradual thinning or decrease in the thickness of the material beginning at the base region 28 and continuing until the material attains sufficient thinness to allow flexible member 30 to move easily.

FIG. 4 shows a panty undergarment 32 which has two supporting panels 36 made of Lycra* or other elastic materials which secure the unit 10 in position during use. Unit 10 is secured to the user's pelvic region, and flexible member 30 is secured in place in crotch opening 37 by supporting panels 36.

*Trademark of I. E. Du Pont de Nemours and Co., Inc.

FIG. 5 shows a belted undergarment 34 with similar securing means for unit 10. It also has supporting panels 36 and crotch opening 37. It is also constructed of a flexible material. Both garments 32 and 34 contain a storage sleeve 38 wherein flexible member 30 is inserted when unit 10 is not being used to urinate. Storage sleeve 38 has inner and outer panels secured together to form a pocket 35. At the base of the pocket 35, immediately above crotch opening 37, is the opening 39 of the pocket 35. Flexible member 30 of unit 10 is inserted into sleeve 38 by adjusting it to the appropriate angle for fitting into sleeve 38.

The user can wear garments 32 and 34 underneath clothing and hold unit 10 in a stored position in sleeve 38 for necessary lengths of time. This may be particularly useful if the female is engaging in driving a vehicle or piloting a small airplane over long distances, or any vocation (or avocation) that puts the user out of touch with bathroom facilities. Because of the portability of the toilet device, it will also be useful in travel, particularly in underdeveloped countries where, very often, the facilities are insufficiently clean or are uncomfortable.

As shown in FIG. 2, the unit can also be equipped with a loop 26 to be used to secure the unit 10 to a hook or other structure used for hanging articles. In its reuseable form, unit 10 can be easily cleaned and hung by loop 26 until the next use.

In another embodiment, the invention is made of paper, a paper-like substance, or similar material which may be disposed of after use.

In operation, the user would secure unit 10 to the pelvic region. The vaginal cover 14 is pressed against the vaginal opening and ridge guide 16 rests against the midline of the lower vagina. Regions 18, 20, 22 and 24 are aligned into their respective positions so that orifice 12 encloses the user's urethral orifice. Member 30 is then adjusted to its desired position and the user either urinates into a urinal, other receptacle, or outdoors as discussed herein. The garments 32 and 34 can be used to secure unit 10 in proper position for use and sleeve 38 thereof can be used to store member 30 while unit 10 is being worn.

Unit 10 can also be utilized with standard, male-type, collection receptacles used to collect urine. It can also be fabricated, as shown in FIG. 6a, as a one-piece, disposable device, consisting of unit 10 attached to a collection receptacle 40. Alternatively, unit 10 and receptacle 40 can be manufactured separately, then joined and packaged as a one-piece unit that can be snapped apart, as shown in FIG. 6b, affer a specimen has been collected. Then, the receptacle only can be sealed by means of the ridge-in-slot type zipper, located at the top of the receptacle. As shown in FIG. 6c, the receptacle 40 has a ridge 42a on one half of the inner surface (near the top) and a slot 42b on the other half. After the specimen has been collected and the receptacle snapped apart from the member 30, the receptacle may be sealed by pressing the ridge 42a of the receptacle 40 into its corresponding slot 42b. When sealed, the top edges of the receptacle are no longer round, but flat like the zip-locking bags.

Similarly, FIG. 7 shows a construction of the anterior surface of flexible member 30 wherein a protuberance 43 on member 30 secures to the walls of receptacle 40, which also can be of flexible material. By compressing the walls of receptacle 40, the anterior end of flexible member 30 is released from receptacle 40 to insert member 30. Its anterior end is compressed for insertion into receptacle 40, and, once the member 30 is firmly in place, the compression is ceased, causing squeeze-lock seal 44.

FIG. 8 shows a dish-shaped head 46 on member 30 to be used to form a seal around the opening of receptacle 40.

FIG. 9 illustrates an embodiment in which member 30 is threaded externally 48a and rotated spirally into the internal corresponding threads 48b in receptacle 40.

FIG. 10 shows an embodiment in which member 30 is threaded internally 49a and rotated spirally onto the external corresponding threads 49b or receptacle 40.

In the above embodiments of FIGS. 8, 9, and 10, the receptacle can be sealed by caps, foil, paper, etc.

The foregoing is considered as illustrative only of the principles of the invention. Furthermore, since numerous modifications and changes will readily occur to those skilled in the art, it is not desired to limit the invention to the exact construction and operation shown and described, and accordingly, all suitable modifications, and equivalents which may be resorted to, fall within the scope of the invention as claimed.

What is claimed is:

1. A contoured, urinary-guide unit device for use by females to dispose of or collect urine having a plurality of contoured regions and, comprising:
   (a) a flexible member have a bore therethrough, said felxible member being acutely angularly extended from the contoured regions of the unitary device;
   (b) an inside surface of said device, having a urethral orifice for approximating the user's external urethral orifice and for passage of urine from the urethra through said flexible member of said device to the outside surface thereof which extends externally therefrom;
   (c) a non invasive vaginal cover located on the interior surface of said device and disposed at a distance beneath said orifice generally equivalent to the distance between the urethra and the vaginal opening of the user, said cover covering the vaginal orifice to prevent urine contamination thereof;
   (d) a base contour region which is generally shaped to extend laterally of the flexible member to conform to the perineum of the female genital anatomy and has a curvature declination as it forms;
   (e) a pubic contour region which is generally shaped to extend at a right angle to the flexible member;
   (f) left and right groin contour regions which are configured and shaped to conform to the left and right areas of the labium majus;
   (g) means providing a vaginal-ridge guide configured to mate with and engage the vagina and formed by the base of the vaginal cover and extending down toward the base contour region of said device, said ridge having an elevation portion which declines dimensionally on each side to adjoin the groin contour regions, pubic contour regions, and base contour region;
   (h) said vaginal cover and vaginal-ridge guide being functional in use to align the external vaginal orifice around the user's urethral orifice;
   (i) said left and right contour regions converging at the orifice, forming a labial contour region which is shaped to surround the labium minus area of the genital region;
   (j) said contour regions being shaped so that in use they conform to the lower vaginal orifice and frenulum of the user;
   (k) said flexible member being constructed and so arranged that passed urine is not stored therein, but passes therethrough for external collection by a suitable receptacle or a disposal device.

2. A urinary-guide unit device as described in claim 1, further comprising a loop extention of the public contour region for securing to a holding or attachment hook.

3. A urinary-guide unit device as described in claim 1, wherein said unit device is secured in position by an undergarment, comprising in combination:
   (a) supporting panels for securing said unit device into position;
   (b) means providing a crotch opening therein for passage of said flexible member of the unit device so that the user can urinate therethrough, without securing the unit device with the user's hand.

4. In combination with a unit device and undergarment as described in claim 3, wherein said undergarment further includes a storage sleeve for storing the flexible member when not in use, said sleeve being substantially rectangular in shape.

5. An undergarment as described in claim 4, wherein said undergarment is a unitary panty undergarment elastomerically secured to the waist of the wearer and having a frontal appendage through which said flexible member angularly protrudes.

6. A urinary-guide unit device as described in claim 1, wherein said unit device is constructed and arranged to be secured to a collection receptacle, as desired; such for example as one containing a ridge-and-slot zipper.

7. A urinary-guide unit device as described in claim 1 wherein said member has a base region thereof adjustable for use or storage of the unit device, said adjustability being derived by a gradual thinning of the material beginning at said base region and continuing until sufficient thinness is achieved to allow said flexible member to move easily.

8. A urinary-guide unit device as described in claim 1, wherein said unit is removably secured to a collection receptacle by a squeeze-lock seal.

9. A urinary-guide unit device as described in claim 1, wherein the member of said unit device has a dish-shaped head for securing to a receptacle.

10. A urinary-guide unit device as described in claim 1, wherein the member of said unit device is externally threaded for securing to an internally threaded receptacle.

11. A urinary-guide unit device as described in claim 1, wherein the member of said unit device is internally threaded for securing onto an externally threaded receptacle.

12. A urinary-guide unit device as described in claim 1 which is attached to a receptacle to form a one-piece device, fracturable at the joint between them.

* * * * *